US012635863B2

(12) United States Patent
Baumann et al.

(10) Patent No.: US 12,635,863 B2
(45) Date of Patent: May 26, 2026

(54) ENDOSCOPY DEVICE AND ENDOSCOPY SYSTEM WITH ANNULAR VIEW

(71) Applicant: KARL STORZ SE & Co KG, Tuttlingen (DE)

(72) Inventors: Harald Baumann, Tuttlingen (DE); Klaus M. Irion, Tuttlingen (DE); Peter Schwarz, Tuttlingen (DE)

(73) Assignee: KARL STORZ SE & Co KG, Tuttlingen (DE)

( * ) Notice: Subject to any disclaimer, the term of this patent is extended or adjusted under 35 U.S.C. 154(b) by 571 days.

(21) Appl. No.: 18/081,364

(22) Filed: Dec. 14, 2022

(65) Prior Publication Data

US 2023/0181014 A1 Jun. 15, 2023

(30) Foreign Application Priority Data

Dec. 15, 2021 (DE) .......................... 102021133248.6

(51) Int. Cl.
*A61B 1/00* (2006.01)
*A61B 1/05* (2006.01)

(52) U.S. Cl.
CPC ...... *A61B 1/00193* (2013.01); *A61B 1/00096* (2013.01); *A61B 1/0011* (2013.01); *A61B 1/05* (2013.01)

(58) Field of Classification Search
CPC ...... A61B 1/00174–00181; A61B 1/05; A61B 1/051; A61B 1/00096; A61B 1/00177; A61B 1/00179; A61B 1/00181; G02B 23/243; G02B 23/2484; G02B 13/06
See application file for complete search history.

(56) References Cited

U.S. PATENT DOCUMENTS

| | | | |
|---|---|---|---|
| 7,744,528 B2 * | 6/2010 | Wallace ................. | A61B 1/303 600/117 |
| 8,636,653 B2 * | 1/2014 | Wilson ............... | A61B 1/00032 250/208.2 |
| 2005/0004474 A1 * | 1/2005 | Iddan ................... | A61B 1/0607 600/476 |
| 2009/0082629 A1 * | 3/2009 | Dotan ............... | A61B 1/00101 600/160 |

* cited by examiner

*Primary Examiner* — Alexandra L Newton
(74) *Attorney, Agent, or Firm* — David N. Villalpando; Jacqueline Cohen

(57) ABSTRACT

An endoscopic device comprising a housing, first imaging means in the housing for detecting light emanating from objects from a predetermined first surrounding region annularly surrounding the endoscopic device and for producing a first image of the first surrounding region, a first image sensor for detecting the first image and for producing a first image signal, a first image sensor for sensing the first image and for generating a first image signal representing the first image, a second imaging means in the housing for sensing light emanating from objects in a predetermined second surrounding region and for generating a second image of the second surrounding region, and a second image sensor for sensing the second image and for generating a second image signal representing the second image. The first imaging device comprises a catadioptric imaging system with a first reflective surface, a second reflective surface, and a light refracting interface.

7 Claims, 5 Drawing Sheets

ENDOSCOPY DEVICE AND ENDOSCOPY SYSTEM WITH ANNULAR VIEW

CROSS REFERENCE TO RELATED APPLICATIONS

This application claims priority to German Patent Application No. 102021133248.6, filed Dec. 15, 2021, and entitled, "Endoskopie-Vorrichtung and Endoskopie-System," which is incorporated herein by reference.

FIELD OF THE INVENTION

The present invention is directed to an endoscopy device and an endoscopy system.

BACKGROUND OF THE INVENTION

Endoscopic devices or endoscopy devices are used for the optical examination of natural and artificial cavities, and often include long and thin rigid or flexible shafts or are embodied endoscopic capsules. A major technical challenge is the optical generation of as sharp an image as possible of a region that is as large as possible surrounding the endoscope, and the direct acquisition of such images or, if necessary, transmission of the images or image data to the proximal end of the shaft.

U.S. Pat. No. 4,566,763 describes a catadioptric lens having a first reflective surface concave to the optical path and a second reflective surface convex to the optical path for imaging a panorama.

In WO 2005/077248 A1 a capsule-shaped endoscope with a multi-part sheath is shown.

U.S. Pat. No. 7,465,271 B2 describes a capsule endoscope having an image capture device directed at a convex reflective mirror to capture an annular surrounding region.

EP 1 868 487 B1 describes an endoscopic video capsule with a swiveling image acquisition system.

U.S. Pat. No. 9,621,825 B2 describes a camera system having multiple pixel arrays on a chip for capturing multiple images.

US 2016/0037082 A1 describes a method for reconstructing images obtained from a multiple camera capsule.

U.S. Pat. No. 5,543,972 describes a device for forming an image of a wall of a borehole in the ground. A camera is directed at a conical mirror surface to capture an image of an annular area around the device.

U.S. Pat. No. 5,710,661 describes an integrated sensor optics for simultaneously detecting a low resolution panorama and a high resolution portion of the panorama. The device comprises a convex, namely conical, annular mirror enclosing a hole and a planar annular folding mirror enclosing a hole.

U.S. Pat. Nos. 6,341,044 B1 and 6,373,642 B1 describe a panoramic imaging arrangement. A catadioptric lens in the form of a section of a shell with a reflecting surface region convex to the beam path throws light from an annular surrounding region to an image sensor. According to U.S. Pat. No. 6,341,044 B1, light from a wide-angle lens can fall on the image sensor through an opening in the reflective surface region.

U.S. Pat. No. 6,597,520 B2 describes a panoramic imaging arrangement. An imaging device consisting of two cemented catadioptric lenses has a first reflective surface area convex to the beam path and a second reflective coated plane surface area and captures light from an annular surrounding area on an image sensor.

US 2003/0191369 A1 describes an omnidirectional endoscope. A mirror convexly curved to the beam path reflects light from objects in an annular region surrounding the distal end of the endoscope into an optical system.

U.S. Pat. No. 7,570,437 B2 describes an omnidirectional imaging and illumination device. A catadioptric lens has two reflective surface regions convex to the beam path.

In US 2011/0196200 A1, an endoscopic imaging system with a mirror convex to the beam path and allowing observation of an annular surrounding area is described.

U.S. Pat. No. 8,496,580 B2 describes an omnidirectional and forward looking imaging device. The device comprises a catadioptric lens having a reflective surface convex to the optical path.

U.S. Pat. No. 8,734,334 B2 describes a device for imaging an internal surface of a body cavity. An auxiliary endoscope exits from a working channel of a forward looking endoscope, which annularly looks sideways and backwards. A distal mirror reflects the side image or the backward looking image to a camera.

In "A novel self-propelled disposable colonoscope is effective for colonoscopy in humans" by Nathan Gluck et al. (Gastrointestinal Endoscopy Volume 83, No. 5: 2016, pages 998-1004), a colonoscope that provides an anterior view and a lateral view into an annular surrounding area is described.

In "Impact of Full Spectrum Endoscopy (Fuse, Endo-Choice) on adenoma detection: a prospective French pilot study" by Jean-Philippe Ratone et al (Annals of Gastroenterology (2017) 30, 1-6), an endoscope for colonoscopy is described. Several cameras are arranged at the distal end of the endoscope, allowing both an anterior and a lateral view.

US 2020/0221941 A1, US 2020/0260938 A1, US 2020/0315435 A1 describe endoscopes each having a forward looking camera and multiple side looking cameras.

One object of the present invention is to provide an improved endoscopic device and system.

BRIEF DESCRIPTION OF THE INVENTION

An endoscopic device comprising a housing, first imaging means in said housing for detecting light reflected, scattered, or emitted from objects in a predetermined first surrounding region annularly surrounding said endoscopic device and for producing a first image of said first surrounding region, a first image sensor for detecting said first image and for producing a first image signal representative of said first image, second imaging means in said housing for detecting light emanating from objects in a predetermined second ambient region and for producing a second image of the second ambient region, and a second image sensor for detecting the second image and for producing a second image signal representing the second image, wherein the first imaging means comprises a catadioptric imaging device having a first reflective surface and a second reflective surface and a light refracting interface.

The endoscopy device is more particularly an endoscope with a long and thin, rigid or partially flexible or completely flexible shaft, the distal end region of which may be inserted through a natural or artificial body opening into a natural or artificial cavity in the body of a human or animal patient. Alternatively, the endoscopy device may be used for industrial purposes in a similar manner. Such industrial endoscopes are often referred to as "borescopes." A proximal end portion of the endoscope remains outside the body to allow manual control of the position and orientation of the distal end portion. The endoscope provides an electronic image signal, or an optical image transmitted by means of a relay lens system or an ordered bundle of optical fibers in the proximal end region.

Alternatively, the endoscopic device is an endoscopic capsule which can be, for example, swallowed whole by a patient and moved and/or oriented in the digestive tract, in particular by his peristalsis and/or magnetic forces.

The first reflecting surface and the second reflecting surface of the catadioptric first imaging device are rotationally symmetrical with respect to the same axis of symmetry, which may simultaneously be the longitudinal and symmetrical axis of the end region or of the entire endoscopic device. The surrounding area detected and imaged by the second imaging device is may be distal to the end region of the endoscopic device.

The first image sensor and the second image sensor are each, for example, CCD or CMOS sensors. The first image sensor and the second image sensor may be formed on the same semiconductor board or on two separate semiconductor boards in a common device package or in two separate device packages.

The second surrounding region may be geometrically similar to the first surrounding region, i.e., also annular. Alternatively, the second surrounding region may be, for example, simply continuous.

More particularly, in an endoscopic device as described herein, the first surrounding region and the second surrounding region are each rotationally symmetric about the same axis of symmetry.

More particularly, the axis of symmetry of the first surrounding region and the second surrounding region is parallel to the longitudinal axis of the end region or the entire endoscopic device.

In an endoscopy device as described herein, the housing includes an annular optically transparent window region for transmitting light emanating from objects in the first predetermined surrounding region.

In an endoscopy device as described herein, the first image sensor and the second image sensor are arranged in particular back to back.

The front side of an image sensor is the side of the surface area under which light sensitive devices or areas (often referred to as pixels) are located, and through which light, passes to those light sensitive devices or areas. In an arrangement of the first image sensor and the second image sensor back to back, their backsides face each other. The back sides may be directly adjacent to each other, more particularly, mechanically connected to each other. Alternatively, for example, a printed circuit board or other structure for electrically connecting and/or mechanically holding the image sensors may be arranged between their rear sides.

In an endoscopy device as described herein, the surface normals of the photosensitive surfaces of the first image sensor and the second image sensor are parallel or substantially parallel to an axis of symmetry of the first surrounding region and/or to the viewing direction of the second imaging device.

In an endoscopy device as described herein, the surface normals of the photosensitive surfaces of the first image sensor and the second image sensor are orthogonal or substantially orthogonal to an axis of symmetry of the first surrounding region and/or to an axis of symmetry of the second surrounding region.

Light from the first imaging device reaches the first image sensor after reflection at a reflecting surface inclined by 45 degrees (and more particularly flat, or alternatively curved) with respect to the axis of symmetry of the first imaging device. Light from the second imaging device reaches the second image sensor after reflection at a reflecting surface inclined by 45 degrees (and flat, or alternatively curved) with respect to the axis of symmetry of the second imaging device. The surface normals of the light-sensitive surfaces of both image sensors can be parallel or orthogonal to each other or enclose any angle.

An endoscopy device as described herein further comprises a line (usually an electronic cable) for transmitting electrical power and/or a control signal to the second image sensor and/or for transmitting the second image signal from the second image sensor, and drive means for moving the line between a first position and a second position, wherein the line visually blocks a portion of the first surrounding area, and wherein the portion of the first surrounding area blocked in the first position of the line and the portion of the first surrounding area blocked in the second position of the line do not overlap.

The line may further be provided and configured for transmitting electrical power and/or a control signal to the second image sensor and/or for transmitting the second image signal from the second image sensor and/or for transmitting electrical power to a light source for generating illumination light.

The first position and the second position of the conduit are offset from each other in the circumferential direction and thus more particularly in a direction orthogonal to the direction in which the conduit extends. The drive device is provided and configured for oscillating (e.g., oscillatingly moving) the conduit between the first position and the second position. The drive device may be provided and configured exclusively for moving the conduit or for moving a larger unit. For example, the drive device is provided and configured for moving a unit comprising the conduit and the first imaging device and optionally additionally the second imaging device and/or the first image sensor and/or the second image sensor.

The oscillation may be synchronized with the acquisition of images by the first image sensor to alternately acquire one or more images in which a first portion of the surrounding area is visually blocked by the conduit and one or more images in which a second portion of the first surrounding area is shadowed by the conduit.

An image processing device, which may be part of or coupled to the endoscopic device, may substitute image data missing from the images acquired when the first portion of the first surrounding region is visually blocked with image data from the images acquired when the second portion of the first surrounding region is visually blocked, and vice versa.

In an endoscopy apparatus as described herein, said first imaging means particularly comprises a catadioptric lens formed by an optically transparent body having a first reflective surface area and a second reflective surface area, said first reflective surface area and said second reflective surface area each being convex with respect to light propagating within said catadioptric lens, wherein an optical path from an object in said predetermined first ambient region to said first image sensor extends from an entrance into said optically transparent body, through a reflection from said first reflective surface and a reflection from said second reflective surface, to an exit from said optically transparent body within said optically transparent body.

The reflective surface areas, since they reflect light within the optically transparent body, cannot become soiled by outside contaminants. Brightness and contrast of the generated image are therefore not subject to degradation due to contamination.

In an endoscopy device as described herein, the second imaging device is a catadioptric imaging device having a first reflective surface and a second reflective surface and a further light refracting interface.

The first reflecting surface and the second reflecting surface of the second imaging device are rotationally symmetrical about an axis of symmetry, which may be parallel to the longitudinal axis or axis of symmetry of the end portion of the endoscopy device and/or parallel to the axis of symmetry of the first reflecting surface and the second reflecting surface. The first imaging device and the second imaging device may be identical devices that are mirror symmetrically arranged.

In an endoscopy device as described herein, the first surrounding region and the second surrounding region overlap.

The overlap region of the first surrounding region and the second surrounding region is more particularly annular. More particularly, the overlap region is directly adjacent to or a short distance from a light entry window of the endoscopy device through which light contributing to the generation of images by the imaging means falls.

In some embodiments, an endoscopic device as described herein further comprises a line for transmitting electrical power and/or a control signal to an image sensor of the endoscopic device and/or for transmitting the image signal from an image sensor of the endoscopic device, wherein the line visually blocks a portion of the first surrounding region and a portion of the second surrounding region, wherein the portion of the first surrounding region visually blocked by the line is circumferentially offset from the portion of the second surrounding region visually blocked by the line.

The line may be provided and configured for transmitting electrical power and/or a control signal to both image sensors and/or for transmitting image signals from both image sensors.

Due to the offset between the part of the first surrounding area visually blocked by the line and the part of the second surrounding area visually blocked by the line, missing image information can be substituted by blending each image insofar as the surrounding areas overlap. In particular, the portion visually blocked by the conduit in the first image may be substituted by image information from the second image, and vice versa. When the first image and the second image are displayed stereoscopically, this substitution may occur in the brain of the person viewing the image. Alternatively, an image processing device, which may be part of or coupled to the endoscopic device, may substitute image information from the second image for the portion of the first image visually blocked by the conduit, and vice versa.

In some embodiments, the endoscopy device as described herein further comprises a drive for moving the first imaging device and the second imaging device a predetermined distance along a predetermined path parallel to an axis of symmetry of the first imaging device and the second imaging device between a first position and a second position.

The drive may allow translational movement of the endoscopy device or its end portion by a predetermined distance. This may allow a predetermined overlap between successively acquired images and subsequently their stitching together to form a complete image of the inner surface of a longer section of the digestive tract or other cavity.

In some embodiments of the endoscopy device as described herein, means for projecting a light pattern onto objects in the first surrounding region is provided.

The means for projecting comprises, for example, a laser diode and/or other light source and an array of prisms and/or other optical means for splitting a light beam produced by the light source into a plurality or many fine light beams that produce the light pattern.

The projected light pattern enables determination of the distance of the surfaces onto which the light pattern is projected by triangulation. For example, the coordinates of light points in the captured image can be used to calculate the distances of the surface areas onto which the light points are projected from the distal end area.

In some embodiments, the endoscopy device as described herein further comprises an optical coherence tomography device for detecting distances of objects from the housing.

The optical coherence tomography device can enable the acquisition of a three-dimensional image comprising, for each image point, not only information on brightness and spectral characteristics, but also on the distance from the end region of the endoscope device. Optical coherence tomography can also be used to detect objects or structures within a body, i.e., beneath a surface of the body. This can enable depth information to be obtained.

An endoscopic device as described herein may further comprise a fluid channel for directing irrigation fluid to the distal end portion of the endoscopic device and/or for drawing a fluid from the distal end portion, and an opening of the fluid channel through which an irrigation fluid can exit the fluid channel or a fluid can enter the fluid channel, wherein the opening is disposed proximal to a light entry surface through which light from an object in the first surrounding region enters the first imaging device.

An endoscopy system includes an endoscopy device as described herein.

An endoscopy system includes an endoscopy device as described herein, and an image processing device for receiving the first image signal from the first image sensor.

An endoscopy system includes an endoscopy device as described herein, and an image processing device for receiving the first image signal from the first image sensor and the second image signal from the second image sensor.

In an endoscopy system as described herein, the image processing means is particularly further provided and adapted for providing a third image signal for controlling a combined display of the first image and the second image, wherein the first image annularly surrounds the second image.

In an endoscopy system as described herein in which a lead visually blocks a portion of the first surrounding area and drive means is provided for moving the lead between a first position and a second position, the image processing means is particularly further provided and adapted for providing a third image signal for controlling a reproduction of an image in which a visually blocked area in a first image acquired in the first position is substituted by an visually unblocked area in a first image acquired in the second position.

In an endoscopy system as described herein, wherein the first environment region and the second environment region overlap, the image processing means is particularly further provided and adapted for providing a third image signal for controlling a stereoscopic rendering of the first image for the left eye and the second image for the right eye of a viewing person and/or for determining a radial distance of an object from the endoscopic device from the positions of the object in the first image and in the second image.

In an endoscopy system as described herein in which a line visually blocks a portion of the first surrounding region and a portion of the second surrounding region, the image processing means is particularly further provided and adapted for providing a third image signal for controlling a reproduction of an image in which a visually blocked region in the first image is substituted by a non-visually blocked region in the second image.

In an endoscopy system as described herein in which a line visually blocks a portion of the first surrounding region and a portion of the second surrounding region, the image processing means is particularly further provided and adapted for providing a third image signal for controlling a reproduction of an image in which a visually blocked region in the first image is replaced by a non-visually blocked region in the second image.

An endoscopy system includes an endoscopy device as described herein, and an image processing device for receiving the first image signal from the first image sensor and determining a radial distance of an object from the distal end portion of the endoscopic device from a position of the light pattern in the first image.

BRIEF DESCRIPTION OF THE DRAWINGS

In the following, embodiments are explained in more detail with reference to the accompanying figures.

DETAILED DESCRIPTION OF THE INVENTION

Figures 1, 2:
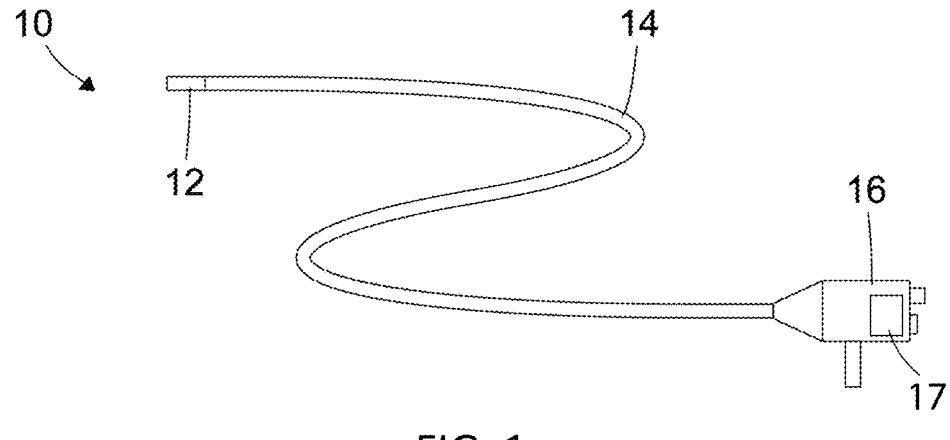
FIG. 1 is a schematic representation of an endoscope.
FIG. 2 is a schematic view of a longitudinal section through the distal end of the endoscope of FIG. 1.

FIG. 1 shows a schematic representation of an endoscope 10 having a distal end 12, a long and thin shaft 14, and a proximal end 16 housing an image processor 17 including image processing circuitry. The shaft 14 may be completely rigid or partially or completely flexible.

Endoscope 10 is an example of an endoscopy device for visually inspecting a natural or artificial cavity in a patient's body or other cavity. Another example of an endoscopy device in which many of the features, characteristics, and functions described below can be realized is an endoscopic capsule, which can be swallowed by a patient, for visually inspecting the internal surface of the digestive tract during passage of the capsule through the digestive tract.

FIG. 2 shows a schematic representation of a longitudinal section through the distal end 12 of the endoscope 10 of FIG. 1. The sectional plane shown includes the longitudinal and symmetrical axis 18 with respect to which the outer surface of the distal end 12 of the endoscope 10 is rotationally symmetrical in the example shown.

The endoscope 10 includes a housing 20 having a distal end portion 22. The housing 20, and in particular the distal end region 22 of the housing 20, may comprise one or more rigid or resilient materials. Portions of the housing may be opaque to light visible to the healthy human eye. However, the distal end portion 22 of the housing 20 includes a first optically transparent window portion 24 that forms an annular band around the housing. An annular first surrounding region 26 externally adjoining the first optically transparent window region 24, that is, the field of view, can be visually detected by means of the endoscope, as described below.

A plurality of first light sources 28 are provided within the distal end region 22 of the housing 20 for generating illumination light, for example broadband light perceived as white by the healthy human eye. Alternatively or additionally, the first light sources 28 or parts thereof are provided for generating excitation light for exciting fluorescence. Illumination light and/or excitation light generated by the first light sources 28 exits the distal end 12 of the endoscope through the first optically transparent window region 24 to illuminate and/or excite fluorescence on or in objects in the first surrounding region 26.

A catadioptric lens 40 is further disposed within the distal end portion 22 of the housing 20. The catadioptric lens 40 comprises a body of glass or other optically transparent material having an annular and curved light input surface 42, an annular and curved first reflective surface area 44, an annular and curved second reflective surface area 46, and a curved and single contiguous light output surface 48. The entire catadioptric lens 40 is rotationally symmetric with respect to the longitudinal and symmetric axis 18 of the distal end portion 22 of the housing 20.

Further provided within the distal end portion 22 of the housing 20 are another lens 50 and a first image sensor 54 having a light sensitive layer 56. The image sensor 54 is, for example, a CCD or CMOS sensor. The light-sensitive layer 56 of the image sensor 54 is arranged at or near a surface of the image sensor 54 facing the further lens 50 and is laterally divided into a plurality of light-sensitive cells or pixels generally arranged in a matrix-like manner.

Illumination light reflected, scattered, or emitted from an object in the first surrounding region 26, may enter the distal end region 22 of the housing 20 through the first optically transparent window region 24. Light entering the interior of the distal end region 22 of the housing through the first optically transparent window region enters the catadioptric lens 40 through the light entry surface 42, is sequentially reflected within the catadioptric lens first at the first reflective surface region 44 and then at the second reflective surface region 46, then exits the catadioptric lens 40 through the light exit surface 48, and is focused into the photosensitive layer 56 of the first image sensor 54 by the further lens 50. Thus, an image of the annular first surrounding region 26 is formed in the light sensitive layer 56 of the first image sensor 54. The first image sensor 54 generates an analog or digital image signal representing this image.

The distal end portion 22 of the housing 20 further includes a second optically transparent window portion 64. In the illustrated example, the second optically transparent window region 64 is provided on a distal end surface of the distal end region 22 of the housing 20. A second surrounding region 66 externally adjacent to the second optically transparent window region 64 may be visually detected by the endoscope as described below.

The distal end portion 22 of the housing 20 further includes a plurality of second light sources 68 for generating illumination light, such as broadband light perceived as white by the healthy human eye. Alternatively or additionally, the second light sources 68 or portions thereof are provided for generating excitation light for exciting fluorescence. In the example shown, the second light sources 68 are disposed on the distal end surface of the distal end portion 22 of the housing 20. Illumination light and/or excitation light generated by the second light sources 68 illuminates objects in the second surrounding region 66 and/or excites fluorescence on or in them.

A further lens 80 forming a second imaging device is further disposed within the distal end region 22 of the housing 22. The second imaging device 80 is disposed proximally of the second optically transparent window region 64.

A second image sensor 84 having a photosensitive layer 86 is further disposed within the distal end portion 22 of the housing 22 and proximal to the second imaging device 80.

The second image sensor 84 is, for example, a CCD or CMOS sensor. The light-sensitive layer 86 of the second image sensor 84 is arranged in particular at or near a surface of the image sensor 54 facing the second imaging device 80 and is laterally subdivided into a plurality of light-sensitive cells or pixels arranged generally in a matrix-like manner.

Electrical lines/leads/conduits 30 (usually referred to as "lines" throughout the disclosure) are further provided within the distal end portion 22 of the housing 22, the distal ends of which are connected to the second image sensor 66, to the first light sources 28, and to the second light sources 68. The lines 30 are provided and configured for transmitting electrical power and control signals to the second image sensor 64, to the first light sources 28, and to the second light sources 68, and for electrically or optically transmitting analog or digital image signals from the second image sensor 64. To this end, proximal ends of the lines 30 may be directly or indirectly connected to a power source and/or light controller and to a camera control unit (CCU).

The lines 30 are arranged laterally of the catadioptric lens 40 between the first optically transparent window region 24 of the housing and the light entrance surface 42 of the catadioptric lens 40. The lines 30 may be concentrated in a single bundle or strand or, as indicated in FIG. 2, may be arranged in multiple, thinner bundles or strands distributed around the circumference of the catadioptric lens 40.

Illumination light reflected, scattered or emitted from an object in the second surrounding region 66 can enter the distal end region 22 of the housing 20 through the second optically transparent window region 64. Light entering the interior of the distal end region 22 of the housing through the second optically transparent window region 66 is focused into the photosensitive layer 86 of the second image sensor 84 by the second imaging device 80. Thus, an image of the second surrounding region 66 is formed in the photosensitive layer 86 of the second image sensor 84. The second image sensor 84 generates an analog or digital image signal representing this image.

In the embodiment shown in FIG. 2, the first image sensor 54 and the second image sensor 84 are arranged back-to-back. The front sides, the surfaces through which light focused by the imaging devices 40, 50, 80 enters the image sensors 54, 85 and reaches the light-sensitive layers 56, 86 of the image sensors 54, 85, are thus parallel to and facing away from each other. Between the rear sides of the image sensors 54, 84, in the embodiment of FIG. 2, a circuit board is indicated by means of which the image sensors 54, 84 are mechanically held and connected.

A drive device 90 is further provided in the housing 20. The housing 20 includes an annular resilient region 92 proximal to the distal end region 22, and a rotational bearing within the annular resilient region 92 that is only indicated in FIG. 2. The annular resilient region 92 and the rotational bearing allow rotation of the distal end region 22 relative to the remainder of the housing 20 about the longitudinal axis 18 and the axis of symmetry within a predetermined angular range of a few degrees. The drive means 90 is provided and configured to oscillatingly rotate the end portion 22 relative to the remainder of the housing 20, such that the end portion 22 alternately assumes two different rotational positions that differ by the predetermined angle.

Alternatively, and in a departure from the illustration in FIG. 2, the entire housing 20 including the distal end region 22 of the housing 20 may be of rigid construction. In this case, the drive means 90 is provided and configured to oscillatingly rotate the lines 30 and optionally all or part of the elements disposed within the distal end region 22 of the housing 20 about the longitudinal and symmetrical axis 18.

A projection device 94 may be further provided in the distal end region 22 for projecting a pattern of light onto objects in the first surrounding region 26. This projection device 94 may occupy a significantly larger spatial area than schematically indicated in FIG. 2. In particular, the projection means 94 may be arranged in an annular region of space or may comprise a plurality of components arranged in a distributed manner to project an extended pattern of light annularly surrounding the distal end region 22.

The projection device 94 may comprise one or more laser diodes and/or other light-emitting diodes or other light sources and one or more light-refracting and/or light-reflecting surfaces, in order to generate a light pattern which, on the one hand, has the highest possible contrast and, on the other hand, is distributed over the largest possible spatial area. The projection device is generally designed to project points or lines onto objects in the first surrounding area 26.

Based on the positions of the light pattern in an image of the first surrounding region 26 captured by the first image sensor 54, the distances of the surface regions onto which the light pattern is projected from the distal end region 22 of the housing 20 can be calculated by triangulation, as is known in the art.

An optical coherence tomography device 96 may be further provided in the distal end region 22 as an alternative or in addition to the projection device 94. The optical coherence tomography device enables optical coherence tomography in the first surrounding region 26 or in a part of the first surrounding region 26 and/or in an adjacent spatial region. Optical coherence tomography can be used to acquire a three-dimensional image not only of a surface of tissue, but also of structures underlying that surface.

Figure 3:
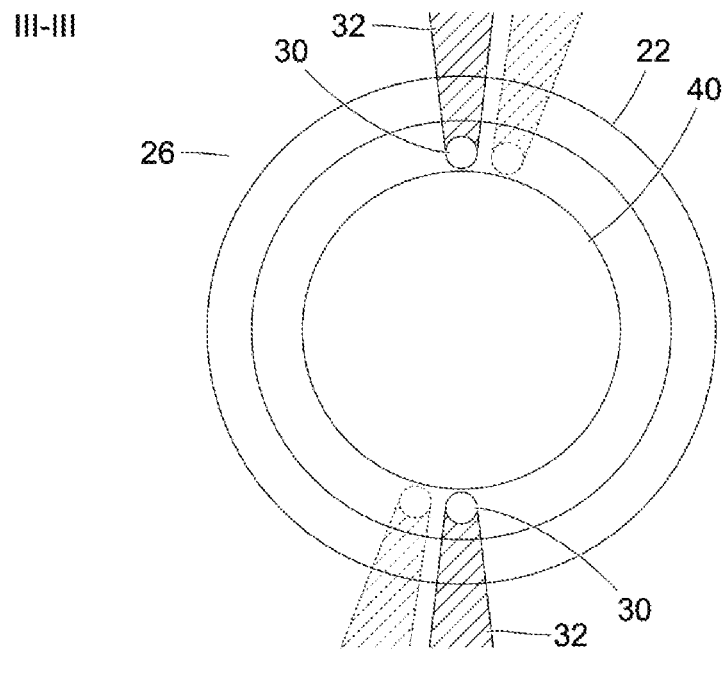
FIG. 3 is a schematic representation of a cross-section through the distal end of the endoscope of FIG. 1 shown in FIG. 2.

FIG. 3 shows a schematic representation of a cross-section through the distal end 12 of the endoscope of FIG. 1, illustrated by reference to FIG. 2. The position of the sectional plane III-III of FIG. 3 is indicated in FIG. 2. The sectional plane III-III of FIG. 3 is orthogonal to the longitudinal and symmetrical axis 18 of the distal end portion 22 of the housing 20.

In FIG. 3, a plurality of bundles or strands of conduits representing lines 30 are shown in solid lines in a first rotational position and in dashed lines in a second rotational position.

In their first rotational positions shown in solid lines, the conduits 30 visually block portions 32 of the first surrounding region 30 outlined and shaded in solid lines. In the image of the first surrounding region 26 produced by the first imaging device comprising the first catadioptric lens 40 and the further lens 50, and captured by the first image sensor 54, the portions 32 of the first surrounding region 26 shown in solid lines are obscured by the lines 30.

In their second rotational positions shown in dashed lines, the lines 30 visually block portions 32 of the first surrounding region 26 outlined and shaded in dashed lines. In the image of the first surrounding area 26 generated by the first imaging device 40, 50 and captured by the first image sensor 54, the portions 32 of the first surrounding region 26 shown in dashed lines are visually blocked/obscured by the lines 30.

The portions 32 of the first surrounding region 26 visually blocked or obscured at the two positions of the lines 30 shown in FIG. 3 do not overlap. As a result, areas obscured in an image captured at the first position can be substituted by areas from the image captured at the second position, and vice versa. In this way, complete images of the first surrounding region 26 can be generated.

Depending on the design of the optical coherence tomography device, portions in the images acquired by the optical coherence tomography device may also be visually blocked or obscured by the lines 30. The oscillating rotation of the distal end portion 22 of the housing or at least of the lines 30 may also allow substitution of occluded portions in the images acquired by the optical coherence tomography device, and thus reconstruction of a complete image.

Figure 4:
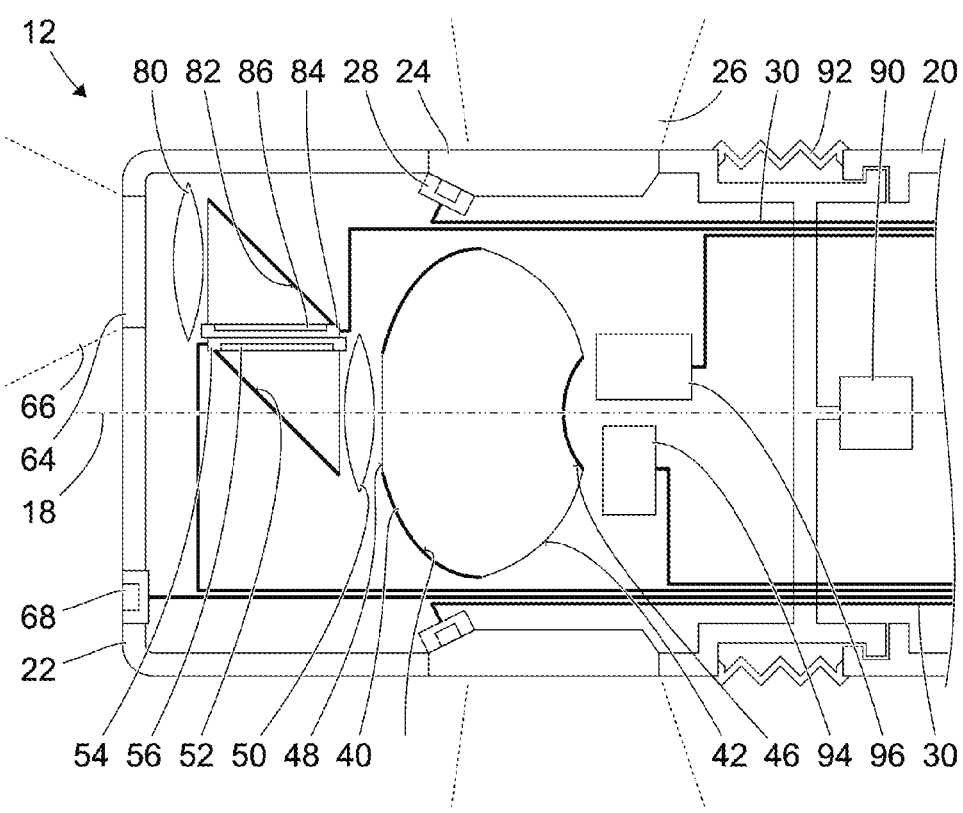
FIG. 4 is a schematic representation of a longitudinal section through a further embodiment of the distal end of the endoscope of FIG. 1.

FIG. 4 shows a schematic representation of a longitudinal section through a further embodiment of the distal end of the endoscope of FIG. 1. The embodiment shown in FIG. 4 is similar in some features, characteristics and functions to the embodiment shown by reference to FIGS. 2 and 3.

As in the embodiment shown by reference to FIGS. 2 and 3, in the embodiment shown in FIG. 4 the image sensors 54, 84 are arranged parallel to each other and back to back. The embodiment shown in FIG. 4 differs from the embodiment shown in FIGS. 2 and 3 particularly in that the light-sensitive layers 56, 86 of the image sensors 54, 84 are not arranged orthogonally, but parallel to the longitudinal and symmetrical axis 18 of the distal end region 22. Light reflecting surfaces 52, 82 reflect light emerging from the imaging devices 40, 50, 80 to the image sensors 54, 84. The light reflecting surfaces 52, 82 may be provided on prisms as indicated in FIG. 4, for example as totally reflecting surfaces. The light reflecting surfaces 52, 82 may be planar as indicated in FIG. 4 or curved in a manner different from that shown in FIG. 4.

Figure 5:
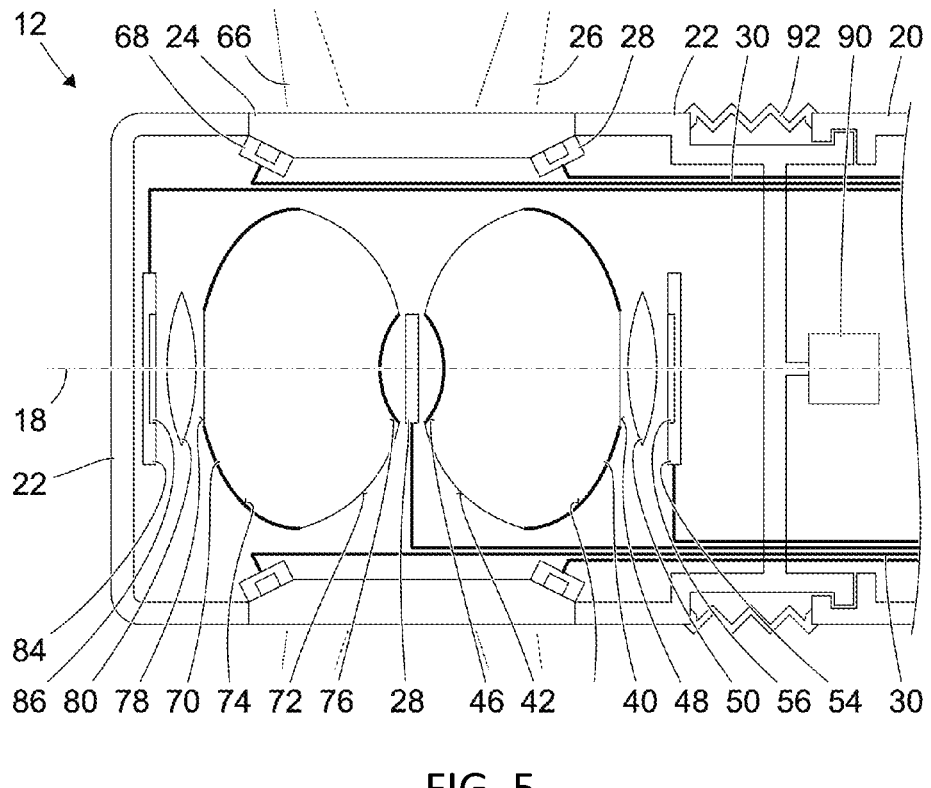
FIG. 5 is a schematic representation of a longitudinal section through a further embodiment of the distal end of the endoscope of FIG. 1.

FIG. 5 shows a schematic representation of a longitudinal section through a further embodiment of the distal end of the endoscope of FIG. 1. The embodiment shown in FIG. 5 is similar in some features, characteristics and functions to the embodiments shown by reference to FIGS. 2 to 4.

As in the embodiments illustrated with reference to FIGS. 2 to 4, two image sensors 54, 84 and two imaging devices 40, 50; 70, 80, each of pair of which generates an image in one of the image sensors 54, 84, are provided. The embodiment shown in FIG. 5 differs from the embodiments shown in FIGS. 2 to 4 particularly in that both imaging devices 40, 50; 70, 80 are of the same or similar design.

Both imaging devices 40, 50; 70, 80 are arranged mirror-symmetrically to a mirror plane orthogonal to the longitudinal and symmetrical axis 18 of the distal end region 22 of the housing 20. Both imaging devices 40, 50; 70, 80 are each rotationally symmetrical with respect to the longitudinal and symmetrical axis 18 of the distal end region 22 of the housing 20. Both imaging devices 40, 50; 70, 80 each comprise a catadioptric lens 40, 70 and a further lens 50, 80. The catadioptric lens 40 of the first imaging device comprises a body of glass or other optically transparent material having an annular and curved light input surface 42, an annular and curved first reflective surface area 44, an annular and curved second reflective surface area 46 and a curved and single contiguous light output surface 48. The catadioptric lens 70 of the second imaging device includes a body of glass or other optically transparent material having an annular and curved light input surface 72, an annular and curved first reflective surface area 74, an annular and curved second reflective surface area 76, and a curved and single contiguous light output surface 78.

In the embodiment shown in FIG. 5, the first surrounding area imaged by the first imaging device 40, 50 and the second surrounding area imaged by the second imaging device 70, 80 are not identical, but overlap.

To the extent that the surrounding areas overlap, the embodiment shown in FIG. 5 allows a stereo image to be captured from an image generated by the first imaging device 40, 50 and captured by the first image sensor 54 and an image generated by the second imaging device 70, 80 and captured by the second image sensor 84. For example, the image captured by the first image sensor 54 is presented to the right eye of the viewer, and the image captured by the second image sensor 84 is presented to the left eye of a viewer.

Alternatively or additionally, an image processing device such as an image processor including image processing circuitry, can determine the distances of structures recognizable in both images by triangulation. Thus, data about the spatial shape of objects, in particular surfaces of objects in the first surrounding area, can be obtained from the two images. Therefore, the embodiment shown in FIG. 5 shows neither a projection device for projecting a light pattern onto objects nor an optical coherence tomography device. However, alternatively and differently from the embodiment shown in FIG. 5, a projection device for projecting a light pattern and/or an optical coherence tomography device may be provided.

In the example shown in FIG. 5, a single optically transparent and annular window region 24 is provided through which light passes to both imaging devices 40, 50; 70, 80. Alternatively, and in contrast to the illustration in FIG. 5, two separate optically transparent and annular window regions 24, 64 may be provided.

A light source 28 is indicated between the two catadioptric lenses 40, 70, which emits illumination light and/or excitation light. Illumination light and/or excitation light generated by the light source 28 exits the housing 20 through the optically transparent window area 24 of the housing 20 and falls on objects in the surrounding areas.

Alternatively to or in addition to the light source 28, further devices may be arranged between the catadioptric lenses 40, 70.

Figure 6:
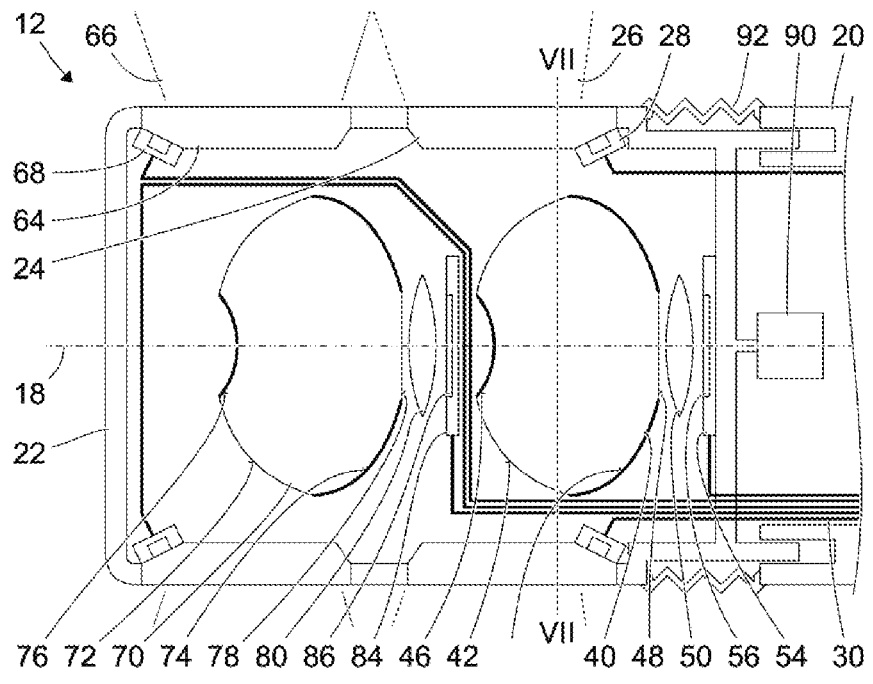
FIG. 6 is a schematic representation of a longitudinal section through a further embodiment of the distal end of the endoscope of FIG. 1.

FIG. 6 shows a schematic representation of a longitudinal section through a further embodiment of the distal end of the endoscope of FIG. 1. The embodiment shown in FIG. 6 is similar in some features, characteristics and functions to the embodiments shown by reference to FIGS. 2 to 5.

As in the embodiment shown in FIG. 5, two identical or similar imaging devices each comprising a catadioptric lens 40, 70 and a further lens 50, 80 are provided in the distal end region 22 of the housing 20 of the embodiment shown in FIG. 6. In contrast to the embodiment shown in FIG. 5, the two imaging devices 40, 50; 70, 80 are not arranged in mirror symmetry. Rather, in both imaging devices, the catadioptric lens 40, 70 is arranged distally of the further lens 50, 80 and the further lens 50, 80 is arranged distally of the image sensor 54, 84.

In a departure from the illustration in FIG. 6, both imaging devices 40, 50; 70, 80 may be arranged in reverse so that in each case the catadioptric lens 40, 70 is disposed proximally of the further lens 50, 80 and the further lens 50, 80 is disposed proximally of the image sensor 54, 84.

Alternatively, and also differing from the illustration in FIG. 6, the imaging devices 40, 50; 70, 80 may be mirror symmetrical and the image sensors 54, 84 may be arranged between the imaging devices 40, 50; 70, 80. In this case, in the first imaging device, the catadioptric lens 40 would be proximal to the further lens 50 and the further lens 50 would be proximal to the first image sensor 54 and in the second imaging device, the catadioptric lens 70 would be distal to the further lens 80 and the further lens 80 would be distal to the second image sensor 84. In this case, the image sensors 54, 84 and one or more light sources 28 may be arranged between the imaging devices 40, 50; 70, 80 and may be integrated, for example, on a circuit board or in a compact assembly.

Deviating from the embodiment shown in FIG. 5, the embodiment shown in FIG. 6 further comprises two optically transparent and annular/circular window areas 24, 64. Light enters the first imaging device 40, 50 through a first optically transparent window region 24, and enters the second imaging device 70, 80 through a second optically transparent window region 64 which is offset proximally.

In contrast to the illustration in FIG. 6, only a single circular and correspondingly wide window area may be provided.

In the embodiment shown in FIG. 6, the lines 30 are not straight throughout. The lines 30 have two straight sections parallel to the longitudinal and symmetrical axes 18, but arranged at different positions in the direction of the circumferences of the catadioptric lenses 40, 70. In the example shown, with respect to the longitudinal and symmetrical axes 18, the position in which the lines 30 pass the first catadioptric lens 40 and the position in which the lines 30 pass the second catadioptric lens 70 are opposite to each other, that is, offset by an angle of 180 degrees.

In the embodiment shown in FIG. 6, a drive device 90 is further provided in the housing 20. However, unlike the embodiments illustrated with reference to FIGS. 1 to 5, the drive device 90 is not provided for rotation but for linear translational movement of the distal end region 22 of the housing 20 in a direction parallel to the longitudinal axis 18 and the axis of symmetry. The housing 20 has an annular elastic region 92 proximal to the distal end region 22. The annular elastic region 92 allows elongation and compression of the housing 20 proximal to the distal end region 22, and thus, when the endoscope is otherwise at rest, translational movement of the distal end 12 in a direction parallel to the longitudinal and symmetrical axes 18. The drive device 90 is particularly provided and configured for oscillatory translation of the distal end region 22 with all devices disposed therein.

Figure 7:
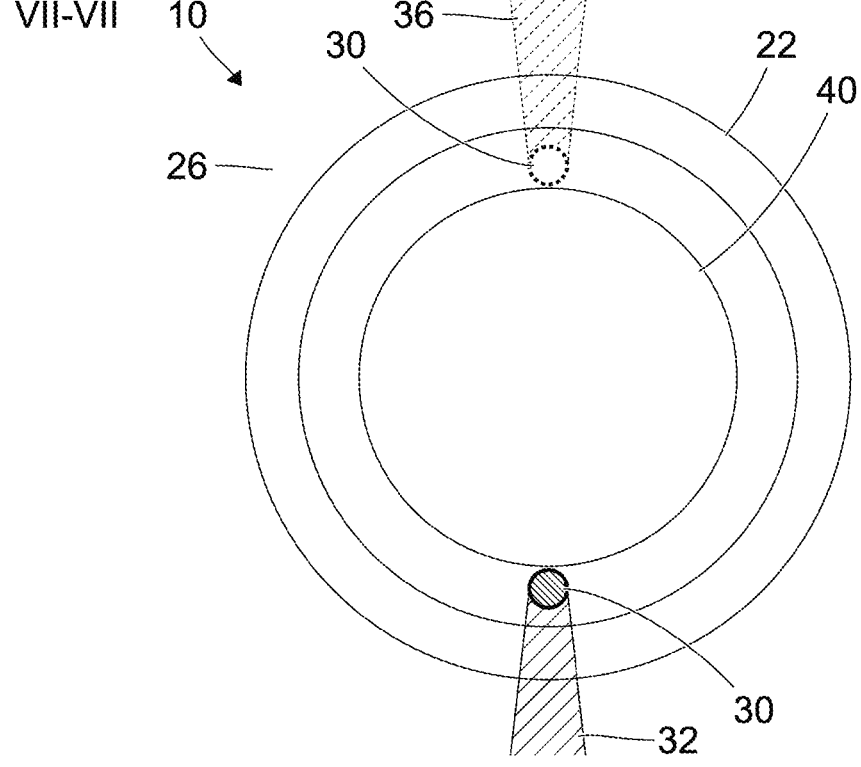
FIG. 7 is a schematic view of a cross-section through the distal end of the endoscope of FIG. 1 shown in FIG. 6.

FIG. 7 shows a schematic representation of a cross-section through the distal end 12 of the endoscope of FIG.

1, illustrated by FIG. 6. The position of the sectional plane VII-VII of FIG. 6 is indicated in FIG. 5. The sectional plane VII-VII of FIG. 7 is orthogonal to the longitudinal and symmetrical axis 18 of the distal end portion 22 of the housing 20.

In FIG. 7, the position where the lines 30 pass the first catadioptric lens 40 is shown in solid line and hatched cross-section and the position where the lines 30 pass the second catadioptric lens 70 is shown in dashed line without hatched cross-section. The portion 32 of the first surrounding region 26 imaged by the first imaging device 40, 50 onto the first image sensor 54 that is visually blocked or occluded by the lines 30 is outlined in solid lines and hatched in FIG. 7. The portion 36 of the second surrounding region 66 imaged by the second imaging device 70, 80 onto the second image sensor 84 that is visually blocked or obscured by the leads 30 is outlined in dashed lines and hatched in FIG. 7.

The area of the first surrounding region 26 occluded by the lines 30 and the area of the second surrounding region 66 occluded by the lines 30 are located at different positions in the circumferential direction. Therefore, in the image of the first surrounding region 26 captured by the first image sensor 54, the occluded region 26 may be substituted by regions from the image of the second surrounding region 66 captured by the second image sensor 85, and vice versa to the extent that the surrounding regions 26, 66 overlap each other. If a plurality of images are captured by both image sensors 54, 84 during a movement of the distal end region 22 of the housing 20 parallel to its longitudinal and symmetrical axis 18, images captured at different times in the same or similar positions of the image sensors may be used for mutual substitution.

To this end, the drive device shown in FIG. 6 can move the distal end region 22 and the devices arranged therein parallel to the longitudinal and symmetrical axis 18, for example by the distance by which the imaging devices 40, 50; 70, 80 are offset from one another. This allows a first image to be captured at a first instant by means of the first imaging means 40, 50 and the first image sensor 54 and a second image of the same surrounding area to be captured at a second instant by means of the second imaging means 70, 80. Since in both images different parts 32, 36 of the surrounding area are obscured by the lines 30, respectively missing areas in one image can be substituted by areas from the other image.

From an endoscope according to one of the embodiments illustrated with reference to FIGS. 1 to 7, many individual images can be acquired which together represent, for example, the entire inner surface of a hollow organ or lumen, such as the human colon. With reference to the schematic representation in FIGS. 8 and 9, the merging of image data is described.

Figure 8:
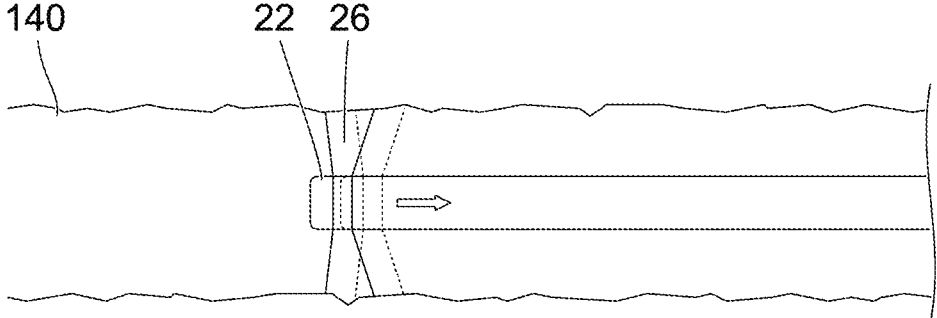
FIG. 8 is a schematic representation of images captured in a hollow organ or lumen.

FIG. 8 shows a schematic representation of the distal end 12 of the endoscope 10 in the embodiment illustrated with reference to FIGS. 2 and 3 in a tubular environment, for example a tubular hollow organ 140, such as the colon, of a patient. Ideally, the distal end 12 of the endoscope 10 is shown centered in and aligned parallel to the hollow organ 140. An arrow indicates movement of the distal end 12 of the endoscope 10 along the hollow organ 140. Solid lines show the position of the distal end of the endoscope 10 and the first predetermined surrounding region 26 at a first point in time, and dashed lines show the position of the distal end of the endoscope 10 and the first predetermined surrounding region 26 at a later, second point in time.

The first predetermined surrounding region 26 at the first point in time shown in solid lines and the second predetermined surrounding region 26 at the second point in time shown in dashed lines are different, i.e., offset from each other, but overlap.

Figure 9:
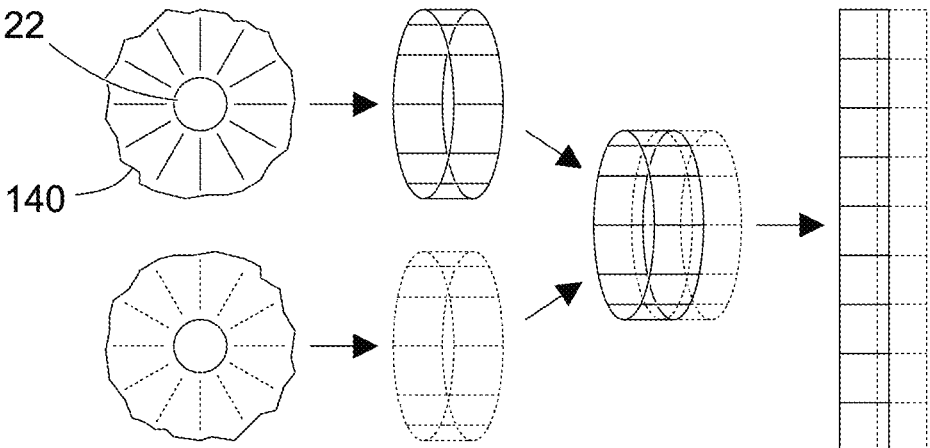
FIG. 9 is a schematic representation of two images and a combination of both images.

The schematic diagram in FIG. 9 describes the merging of image data acquired at the first point in time and at the second point in time.

In FIG. 9, at the far left, the distal end of the endoscope 10 and the hollow member 140 are shown in cross-section. At the far upper left is shown the cross-section with the first predetermined surrounding region at the first point in time—indicated by solid radial lines. At the far left bottom, the cross-section is shown with the first predetermined surrounding region at the second point in time—indicated by dashed radial lines.

In FIG. 9, second from the left, the captured annular image of the first predetermined surrounding area is shown, above in solid lines the image captured at the first time and below in dashed lines the image captured at the second time.

FIG. 9, third from the left, shows the merging of image data. From the image data representing the image acquired at the first time and shown in solid lines and the image data representing the image acquired at the second time and shown in dashed lines, image data representing a composite, larger image, namely an image of a larger area, is generated. For this purpose, motion data obtained or calculated from the motion signal of a motion sensor may be used, for example. Alternatively or additionally, objects or structures visible in both images acquired at different times are identified to determine the overlapping area.

FIG. 9 on the far right shows a representation of the inherently ring- or tube-shaped image in a plane, for example on a screen. The ring- or tube-shaped image is displayed as cut open lengthwise and unrolled into a plane.

REFERENCE SIGN

10 Endoscope as an example of an endoscopy device
12 distal end of the endoscope 10
14 Endoscope shaft
16 Proximal end of endoscope 10
18 Symmetry axis
20 Shaft housing
22 distal end area of the housing 20
24 first optically transparent window area of the housing 20
26 first predetermined surrounding region of distal end portion
28 first light source of the endoscope 10
30 Line/lead/electrical conduit for transmitting electrical power, control signals, and/or a video signal
32 Part of first surrounding region 26 shaded by line 30
36 Part of second surrounding region shaded by line 30
40 (first) catadioptric lens of a first imaging device
42 Curved light entrance surface of the (first) catadioptric lens 40
44 first reflective surface area of the (first) catadioptric lens 40
46 second reflective surface area of the (first) catadioptric lens 40
48 Light-emitting surface of the (first) catadioptric lens 40
50 further lens of the first imaging device
52 Reflective surface
54 First image sensor of the endoscope 10
56 photosensitive layer of the first image sensor 50
58 Board
64 second optically transparent window area of the housing 20

66 second predetermined surrounding area of distal end portion 22
68 second light source of the endoscope 10
70 second catadioptric lens of a second imaging device
72 Curved light entrance surface of the second catadioptric lens 70
74 first reflective surface area of second catadioptric lens 70
76 second reflective surface area of second catadioptric lens 70
78 Light-emitting surface of the second catadioptric lens 70
80 (further) lens of the second imaging device
82 Reflective surface
84 Second image sensor of the endoscope 10
86 photosensitive layer of the second image sensor 84
90 Drive device for moving the distal end portion 22
92 Elastic area of the housing 20
94 Projection device for projecting a light pattern onto objects in the first surrounding region 26
96 Optical coherence tomography device
140 Hollow organ/lumen

The invention claimed is:

1. An endoscopy apparatus, comprising:
a housing positioned at a distal end of an endoscopic shaft and a line for transmitting at least either electrical power or a control signal from a proximal end of the shaft to the distal end portion of the shaft;
a first imaging means comprising at least a catadioptric imaging device having a first reflective surface and a second reflective surface and a light refracting interface, and a first image sensor, the first imaging means disposed in an end portion of said housing and configured to collect light reflected, scattered, or emitted from objects in a predetermined first surrounding region annularly surrounding the distal end portion of the endoscopic shaft and configured to generate a first image of said first surrounding area, and said first image sensor is configured to capture said first image and generate a first image signal representing said first image; and
a second imaging means comprising at least a lens configured to gather light and a second image sensor, the second imaging means disposed in said end portion of said housing and configured to collect light reflected, scattered, or emitted from objects in a predetermined second surrounding region, and configured to generate a second image of said second surrounding region, and said second image sensor is arranged back-to-back with the first image sensor and configured to capture said second image and generate a second image signal representing said second image.

2. The endoscopic device of claim 1, wherein the first catadioptric imaging device comprises a catadioptric lens with an optically transparent body, having a first reflective surface region and a second reflective surface region, wherein the first reflective surface region is concave and the second reflective surface region is convex relative to light propagating within the catadioptric lens, and an optical path from an object in the predetermined first surrounding region to the first image sensor extends from an entrance into the optically transparent body of the catadioptric lens with a reflection at the first concave reflecting surface, a reflection at the second convex reflecting surface, and an exit from the optically transparent body of the catadioptric lens.

3. The endoscopy device of claim 1, further comprising:

a projector configured to project a light pattern onto objects in the first surrounding region.

4. The endoscopy device of claim 1, further comprising an optical coherence tomography device positioned in the distal end portion of the shaft.

5. An endoscopy system comprising:

The endoscopy device of claim 1; and an image processor for receiving the first image signal from the first image sensor and the second image signal from the second image sensor.

6. The endoscopy system of claim 5 further comprising a projector configured to project a light pattern onto objects in a surrounding region.

7. The endoscopy system of claim 5 further comprising an optical coherence tomography device positioned in the distal end portion of the shaft.

\* \* \* \* \*